US006346258B1

(12) United States Patent
Kramer

(10) Patent No.: US 6,346,258 B1
(45) Date of Patent: Feb. 12, 2002

(54) PHYSIOLOGICAL COMBINATION OF ACTIVE SUBSTANCES TO ENHANCE THE SKIN'S DEFENSES AGAINST NOXIOUS AGENTS

(76) Inventor: Axel Kramer, Georg-Engel-Strasse 20, D-17489 Greifswald (DE)

( * ) Notice: Subject to any disclaimer, the term of this patent is extended or adjusted under 35 U.S.C. 154(b) by 0 days.

(21) Appl. No.: 09/445,579
(22) PCT Filed: Jun. 16, 1998
(86) PCT No.: PCT/EP98/03615
§ 371 Date: Dec. 13, 1999
§ 102(e) Date: Dec. 13, 1999
(87) PCT Pub. No.: WO98/57614
PCT Pub. Date: Dec. 23, 1998

(30) Foreign Application Priority Data

Jun. 17, 1997 (DE) .......................... 197 25 405

(51) Int. Cl.⁷ .............................. A61K 6/00; A61K 7/00
(52) U.S. Cl. .................. 424/401; 424/400; 424/450; 424/65
(58) Field of Search .................. 424/65, 76.1, 76.2, 424/401, 450; 514/499

(56) References Cited

U.S. PATENT DOCUMENTS

| 3,384,548 A | | 5/1968 | Zvalk et al. | |
| 5,676,936 A | * | 10/1997 | Park | 424/65 |
| 6,051,250 A | * | 4/2000 | Ribier et al. | 424/450 |

FOREIGN PATENT DOCUMENTS

| CH | 230366 | 3/1944 |
| DE | 3210138 | 3/1982 |
| DE | 3506576 | 2/1985 |
| DE | 3538412 | 10/1985 |
| DE | 3603859 | 2/1986 |
| DE | 4003750 | 2/1990 |
| DE | 4134888 | 10/1991 |
| DE | 4322395 | 7/1993 |
| DE | 4431251 | 9/1994 |
| DE | 4341001 | 12/1999 |
| FR | 2168202 | 1/1972 |

OTHER PUBLICATIONS

Rohde, "Harnstoff und Harnstoffkombinationen bei *Psoriasis*," (Summary in English) in *Hautarzt*, 40, Suppl. 9, S74–75.

Grunewald, et al. "Barrier Creams, Commerically Available Barrier Creams versus Urea– and Glycerol–containing Oil–in–Water Emulsions," *Dermatosen*, 43:69–74, (1995).

Kramer, et al., "Advancement of Growth of the Hair at Guinea Pig by Sodium Thiocyanate," *Dermatol. Mon.schr.*, 176:417–420, (1990).

Hibbert, et al., "Variation in Measures of Urea Kinetics Over Four Years in a Sinle Adult, "*European Journal of Clinical Nutrition*, 45:347–351, (1991).

Elsner, et al., "Der Hautschutz in der Prävention der Berufsdermatosen," *Deutsches Ärzteblat*, 94:A1489–A1492, (1977).

Rabb, ed., "Urea in Dermatology," Int'l. Symp., in *Der Hautarzt*, 40, Suppl. 9 (1989).

Gessner, Portektive Wirking von Thiocyanat, Harnstoff und Allantoin einzeln und in Gemischen bei standardisierter Irritation im Huhnereitest an der Chorioallantoismembran (HETCHAM); Inaugural Dissertation, Aus dem Institut fur Hygiene und Umweltmedizin der Medizinischen Fakultat deer Ernst–Moritz–Arndt–Universitat Greifswald.

* cited by examiner

Primary Examiner—Thurman K. Page
Assistant Examiner—Charesse L. Evans
(74) Attorney, Agent, or Firm—Brobeck, Phleger & Harrison, LLP

(57) ABSTRACT

The present invention relates to a combination of active substances for enhancing the skin's defense against chemical and physical irritations, for example, from job-related stress, strain on the skin from leisure activities (bathing, showering, sun exposure, household chemicals, building materials, etc.) and from the working environment.

The topical agent comprises ionically bound and/or free thiocyanate ions and urea in addition to per se known auxiliary agents and carriers.

10 Claims, No Drawings

PHYSIOLOGICAL COMBINATION OF ACTIVE SUBSTANCES TO ENHANCE THE SKIN'S DEFENSES AGAINST NOXIOUS AGENTS

The present invention relates to a combination of active substances for enhancing the skin's defense against chemical and physical irritations, for example, from job-related stress, strain on the skin from leisure activities (bathing, showering, sun exposure, household chemicals, building materials, etc.) and from the working environment.

A large number of skin protection agents has been used for skin protection for decades, without any experimental evidence of their effectiveness. Usually, skin protection is achieved by an exposure barrier, sometimes in connection with an increase of skin moisture, rather than by enhancement of the barrier function and the defense of the skin against irritations by biochemical means (Elsner P., Wigger-Alberti W. (1997), Der Hautschutz in der Prävention der Berufsdermatosen, Dt. Ärzteblatt 94; 17-1489-A-1492).

For the active substance rhodanide (thiocyanate), a number of applications involving biological effects on the cutaneous system have been established experimentally. Kramer A.: Prüf-system zur Erfassung der Verträglichkeit antimikrobiell wirksamer Stoffe und Zubereitungen zur episomatischen Applikation durch in-vitro- und tierexperimentelle Tests (Episomatiktest) und toxikohygienische Bewertung als Bestandteil krankenhaushygienischer Aufgabenstellungen; Diss. B. Med. Fak. Univ. Greifwald (1985), describes the accelerated closing of skin wounds. DE 41 34 888 A describes the accelerated healing of UV-induced erythema (sunburn).

A. Kramer, W. Weuffen, S. Minnich, S. Koch, M. Minnich, H. Below, B. Thürkow and H. Meffert (1990), Förderung der Haarentwicklung durch Thiocyanat beim Meerschweinchen; Dermatol. Mschr. 176: 417–420, describe the growth enhancement of integumentary appendage (hair).

Also for the active substance urea, a number of effects have been known, i.e., the following (Wohlrab W. (1989), Bedeutung von Harnstoff in der externen Therapie, Hautarzt 40, Suppl. 9: 35–41), the respective application ranges for the following effects of urea not remaining under 2% by weight: hydration of the Stratum corneum, keratolytic properties, acceleration of penetration, inhibition of epidermal proliferation (basal cells), a small extent of antimicrobial activity, antipruriginous effect, proteo- and mucolytical activities and buffering effect (regulation of the hydrolipid coat).

The following therapeutically useful effects result from these properties of urea (Raab W. (1989), Biochemie, Pharmakologie und Toxikologie von Harnstoff; Hautarzt 40, Suppl. 9: 23–26): hydration of the Stratum corneum, keratolysis of diseased nails, desquamation, reduction of excessive cell divisions, alleviation of itching, saving of preservatives from antimicro-bial effect and improvement of the penetration of incorporated pharmaceuticals.

In modern dermatotherapy, urea is successfully employed as a single drug or as an additive in the healing phase of dermatoses. As a single drug, urea is employed for eczemas of dry skin, for desquamative lesions, for hyperkeratoses and for many other chronical dermatoses (Swanbeck G. (1989), Harnstoff als Monotherapeutikum bei trockener Haut; Hautarzt 40, Suppl. 9: 42–43). In topical dermatological preparations, urea is often combined with glucocorticoids (Drosner M. (1989), Harnstoff in Kombination mit Kortikosteroiden zur Therapie von Ekzemen; Hautarzt 40, Suppl. 9: 47–50), with dithranol (Przybilla B., Kaudewitz P., Biber K. (1989), Harnstoff in Kombination mit Dithranol zur Therapie der Psoriasis vulgaris; Hautarzt 40, Suppl. 9: 54–57), with tretinoin (Müller K. H., Pflugshaupt Ch. (1989); Harnstoff in der Dermatologie; Hautarzt 40, Suppl. 9:16), and with salicylic acid (Gabard B., Bieli E. (1989); Salicylsäure und Harnstoff—mögliche Beeinflussung der keratolytischen Wirkung von Salicylsäure durch Harnstoff; Hautarzt 40, Suppl. 9: 71–73). For neurodermitis, Psoriasis vulgaris and disturbed hornification (Raab, supra), the regular application of urea-containing topical preparations is recommended for the rehabilitation of the skin and for the prophylaxis of skin lesions, as well as for dry-lipopenic skin condition. As cannot be expected otherwise, from its physiological occurrence in the organism (Hibber J. M., Jackson A. A. (1991); Variation in measures of urea kinetics over four years in a single adult; Europ. J. Clin. Nutr. 45: 347–351), urea is well tolerated epidermally. A sensitizing potency or other side-effects of urea have not been detected (Ashton H., Frenk E., Stevenson C. J. (1971); Urea as a topical agent; Brit. J. Derm. 84: 194–196; Wozniak K. D. (1975); Hauttestungen verschiedener Harnstofftypen; Derm. Mschr. 161: 687).

U.S. Pat. No. 3,384,548 employs urea (from 2 to 7.5% by weight) and thiocyanate ions (4% by weight) as a swelling agent for the depilation of hair.

DE 43 41 001 A1 mentions a urea content of from 0.1 to 10% by weight for moisture absorption.

However, an anti-irritative activity in a narrower sense has not been known for urea and cannot be derived from the available results.

It has been the object of the invention to provide novel effective agents for the prophylaxis of skin lesions, achieved through a physiological skin protective activity using biochemical means, with the simultaneous stimulation of healing and repair processes, so that the overall effect is a revitalizing skin protection.

This object has been achieved by a combination of ionically bound and/or free thiocyanate ions with urea in addition to per se known carriers and auxiliary agents. Both thiocyanate and urea are physiological substrates which occur in various compartments in the human organism; according to the invention, they are employed within a physiological concentration range in the combination of active substances.

The surprising property of this combination of active substances is the fact that, if their application precedes an irritation, they significantly suppress the manifestation of such irritation, in contrast to known antiphlogistics, which can only affect diseased tissues. Such a mode of action has not been known to date.

It is particularly preferred according to the present invention that the thiocyanate ions are in the form of alkali metal salts including ammonium salts and their derivatives. Thus, these are ionizable thiocyanates as opposed to covalently bound organic thiocyanates. It is particularly preferred according to the present invention that the alkali metal salts of said thiocyanates are selected from sodium, potassium and ammonium thiocyanates.

According to the present invention, it is particularly preferred that the agents contain from 0.01% to 1% by weight of thiocyanate ions and from 0.1% to 10% by weight, especially upto 1% by weight, of urea. In addition to the active ingredients thiocyanate and urea, the agents according to the invention contain usual auxiliary agents and carriers for ointments, creams, emulsions or lotions of w/o and o/w types or aqueous solutions.

They are known, for example, from H. P. Fiedler, Lexikon der Hilfsstoffe für Pharmazie, Kosmetik und angewandte Gebiete, 4th edition (1996), and according to the invention, they are not to alter or at least not to adversely affect the behavior of active substances applied to the skin. The same applies to the carriers. According to the present invention, it is particularly preferred that the weight ratio of thiocyanate ions to urea is from 1:10 to 1:50.

According to the present invention, the term "urea" is used to include per se known urea derivatives, such as monoacetylurea.

On the basis of additive combination effects, the combination of thiocyanate and urea according to the invention resulted in the surprising skin protective effect of the combination of substances against noxious agents or the above mentioned stresses, the known effect of thiocyanate having been surprisingly improved by combining it with urea. With the present invention, the possibility of an extensive mode of action of a revitalizing skin protection has been realized.

One particular embodiment of the invention is the use of the above defined agents for enhancing the skin's defenses against chemical and physical irritations, especially from job-related stress, strain on the skin from leisure activities and from the working environment. Thus, the combination of active substances according to the invention serves, in particular, for the preventive protection against aggressive media in the workaday routine as well as in the handling of protective media against external influences on the skin.

EXAMPLES

Example 1

Evidence of the activity in terms of enhancing the skin's defenses against noxious agents was furnished in a hen's egg test on the chorioallantoic membrane (HET-CAM), an established predictional test for detecting the irritation potency for the skin and mucosa.

For testing, eggs of the race "American White Leghorn" (Shaver Starcross 288) were employed. The eggs were incubated for 9 d (start of incubation=day 1) in a small-size motor incubator having an automatic turning over device and an automatic moisturizing control (type KMB F/2, EHRET GmbH) at 37±1° C. and 65±5% of relative humidity. At day 9, the eggs were transilluminated for detecting fertilization, the non-fertilized eggs were sorted out, the remaining eggs were placed upright with the blunt pole (air bubble) up and incubated for another 24 h without turning over. At day 10, the egg pole was removed with fine scissors and tweezers, and the chorioallantoic membrane exposed.

The following items were tested:
  irritant effect of the combination of active substances and its components
  protective effect Thus, 0.2 ml each of the aqueous solution of the test substance was applied, and after an interval of 5 min, 0.2 ml of a 2% solution of the irritant sodium dodecylsulfate was applied. The outcome of the response was compared to the effect obtained with water (placebo) according to the following rating:

0 no response
  1 hyperemia—slight
  2 hyperemia—medium
  3 hyperemia—strong
  4 hemorrhage—isolated
  5 hemorrhage—frequent
  6 hemorrhage—massive
  7 coagulation In parallel runs, sodium chloride in concentrations of 0.05% by weight, 0.5% by weight and 1.0% by weight, calcium chloride at 0.05% by weight, 0.5% by weight and 5% by weight, and sorbitol at 0.01% by weight, 0.1% by weight and 1% by weight were tested as further active substances.

$NaCl$, $CaCl_2$ and sorbitol did not display any protective effects, especially no preventive effect, and their effects were not any different from that of distilled water. Distilled water itself had no influence on the response to sodium dodecylsulfate also then the latter was applied 5 min thereafter, as compared to he application of sodium dodecylsulfate alone (medians identical in both cases for all durations of action).

Both thiocyanate alone and, to a somewhat lesser extent, urea alone display a skin protective activity which is surprisingly outperformed in a significant way by a combination of the two active ingredients, as can be seen from Table 1.

TABLE 1

Skin protective effect according to the above rating for the subsequent action of the irritant 2% sodium dodecylsulfate (the interval between the application of the test substance and the action of the irritant was 5 min)

| Examples | | Number of eggs examined | Response (x) after | | |
|---|---|---|---|---|---|
| | test substance | | 30 s | 2 min | 5 min |
| Comp. 1 | dist. water | 96 | 3.8 | 4.9 | 5.6 |
| Comp. 2 | 0.03% by weight NaSCN | 6 | 2.8 | 3.1 | 3.8 |
| Comp. 3 | 0.5% by weight urea | 6 | 2.8 | 3.6 | 4.0 |
| 1 | 0.03% by weight NaSCN + 0.5% by weight urea | 6 | 1.8 | 2.8 | 3.3 |

$$\overline{X} = \frac{\Sigma \text{ of the outcomes of the response per egg}}{\text{number of eggs}}$$

What is claimed is:

1. A method for enhancing the skin's defenses against chemical and physical irritations comprising applying topically ionically bound and/or free thiocyanate ions and urea in combined amounts sufficient to suppress manifestation of such irritation, and to enhance the skin's defenses against chemical and physical irritations.

2. The method according to claim 1, characterized in that said thiocyanate ions are in the form of alkali metal salts including ammonium salts and their derivatives.

3. The method according to claim 2, characterized in that the alkali metal salts of said thiocyanates are selected from the group consisting of sodium, potassium and ammonium thiocyanates.

4. The method according to claim 1, comprising from 0.1 to 10 g of thiocyanate ions per kg of agent.

5. The method according to claim 1, comprising from 1.0 to 100 g of urea per kg of agent.

6. The method according to claim 1, comprising from 1.0 to 10 g of urea per kg of agent.

7. The method according to claim 1, characterized in that the weight ratio of thiocyanate ions to urea is from 1:10 to 1:50.

8. The method according to claim 1, comprising ointments, creams, emulsions, lotions and aqueous solutions.

9. The method of claim 1, wherein the chemical and physical irritations are selected from the group consisting of job-related stress, strains on the skin from leisure activities and strains on the skin from the working environment.

10. The method according to any one of claims 2–9, wherein ionically bound and/or free thiocyanate ions and urea are applied prophyllactically to enhance the skin's defenses against chemical and physical irritations.

* * * * *